(12) United States Patent
Pol et al.

(10) Patent No.: US 9,709,484 B2
(45) Date of Patent: Jul. 18, 2017

(54) APPARATUSES AND METHODS FOR PERFORMING A LIGHT-ABSORPTION MEASUREMENT ON A TEST SAMPLE AND A COMPLIANCE MEASUREMENT ON A REFERENCE SAMPLE

(71) Applicant: Mettler-Toledo AG, Greifensee (CH)

(72) Inventors: Tomasz Pol, Severna Park, MD (US);
Chun-Hung Kuo, Alexandria, VA (US);
William Alan Marks, Woodbine, MD (US)

(73) Assignee: METTLER-TOLEDO GMBH, Greifensee (CH)

( * ) Notice: Subject to any disclaimer, the term of this patent is extended or adjusted under 35 U.S.C. 154(b) by 36 days.

(21) Appl. No.: 14/840,516

(22) Filed: Aug. 31, 2015

(65) Prior Publication Data
US 2017/0059478 A1    Mar. 2, 2017

(51) Int. Cl.
*G01N 21/27* (2006.01)
*G01N 21/31* (2006.01)
*G01N 21/90* (2006.01)

(52) U.S. Cl.
CPC .......... *G01N 21/276* (2013.01); *G01N 21/274* (2013.01); *G01N 21/31* (2013.01);
(Continued)

(58) Field of Classification Search
CPC ............. G01N 21/3504; G01N 21/359; G01N 21/3563; G01N 21/3577; G01N 21/276;
(Continued)

(56) References Cited

U.S. PATENT DOCUMENTS 3,847,486 A * 11/1974 McCabe ............. G01N 21/272
                                                356/246
3,854,050 A * 12/1974 Peterson ............ G01N 21/6486
                                                250/252.1
(Continued)

FOREIGN PATENT DOCUMENTS

EP          0417884 A2    3/1991
JP      2001-356090 A    12/2001
(Continued)

OTHER PUBLICATIONS

International Search Report and Written Opinion of the International Searching Authority (Forms PCT/ISA/220, PCT/ISA/210 and PCT/ISA/237) issued on Sep. 30, 2016, by the International Bureau of European Patent Office in corresponding International Application No. PCT/EP2016/069709. (13 pages).
(Continued)

*Primary Examiner* — Sang Nguyen
(74) *Attorney, Agent, or Firm* — Buchanan Ingersoll & Rooney PC

(57) ABSTRACT

Apparatuses and methods are disclosed for performing a light-absorption measurement on a test sample and a compliance measurement on a reference sample. A method includes moving a reference sample receptacle carrier of an apparatus to position a first reference sample receptacle received in the carrier at a second position in a light path, directing light from an illumination system to a detection system along the light path to perform a light-absorption measurement on a first reference sample at the second position, moving the carrier to position the first receptacle out of the light path, placing a test sample receptacle in a test sample receptacle holder of the apparatus in the light path at a first position different from the second position, and directing light along the light path to perform a light-
(Continued)

absorption measurement on a test sample in the test sample receptacle holder at the first position.

19 Claims, 4 Drawing Sheets

(52) U.S. Cl.
CPC ........... *G01N 21/278* (2013.01); *G01N 21/90* (2013.01); *G01N 2021/3137* (2013.01); *G01N 2201/061* (2013.01); *G01N 2201/068* (2013.01); *G01N 2201/08* (2013.01)

(58) Field of Classification Search
CPC ....... G01N 2201/061; G01N 2201/068; G01N 2201/08
See application file for complete search history.

(56) References Cited

U.S. PATENT DOCUMENTS

| | | | | |
|---|---|---|---|---|
| 4,090,789 | A * | 5/1978 | Macemon | G01N 21/253 250/458.1 |
| 4,318,618 | A * | 3/1982 | Ohtake | G01N 21/253 356/435 |
| 5,381,971 | A * | 1/1995 | Rehmer | B02C 13/288 241/194 |
| 5,585,635 | A * | 12/1996 | Graham | G01N 21/3504 250/343 |
| 6,188,812 | B1 * | 2/2001 | Kao | G01N 21/648 356/128 |
| 6,359,689 | B1 * | 3/2002 | Stansell | G01N 21/253 356/246 |
| 7,890,285 | B2 | 2/2011 | Manfredi | |
| 8,218,142 | B2 * | 7/2012 | Wilcken | G01J 3/02 356/326 |
| 8,467,988 | B1 | 6/2013 | Röder et al. | |
| 2006/0055932 | A1 | 3/2006 | McCandless | |
| 2011/0299084 | A1 | 12/2011 | Feitisch et al. | |
| 2012/0162651 | A1 | 6/2012 | Glover | |
| 2013/0265568 | A1 * | 10/2013 | Micheels | G01N 21/359 356/51 |
| 2014/0300894 | A1 * | 10/2014 | Arimoto | G01N 21/0303 356/246 |

FOREIGN PATENT DOCUMENTS

| | | |
|---|---|---|
| JP | 2005-164375 A | 6/2005 |
| WO | WO 03/078945 A1 | 9/2003 |
| WO | WO 2013/112192 A1 | 8/2013 |
| WO | WO 2013/163268 A1 | 10/2013 |

OTHER PUBLICATIONS

Biodesix, "Blodesix Receives Patent for System That Validates Mass Spectrometer Performance", Aug. 2013, 2 pages.

Shimadzu, "Automated Instrument Validation Using Software", 1 page.

Thermo Scientific, "Thermo Orion AquaMate 7000 Vis Spectrophotometer", 3 pages.

* cited by examiner

APPARATUSES AND METHODS FOR PERFORMING A LIGHT-ABSORPTION MEASUREMENT ON A TEST SAMPLE AND A COMPLIANCE MEASUREMENT ON A REFERENCE SAMPLE

FIELD

The present disclosure relates to apparatuses and methods for performing a light-absorption measurement on a test sample and a compliance measurement on a reference sample, including, but not limited to, performing a spectroscopic measurement or a photometric measurement on a test sample or on a reference sample.

BACKGROUND INFORMATION

International Patent Application No. WO 2003/078945 A1 to Woolfrey (Woolfrey) describes the dual-beam calibration of a spectrometer. A laser beam is normally directed toward sample focusing optics, and is diverted away from its normal path to illuminate a first reference source.

International Patent Application No. WO 2013/163268 A1 to Workman (Workman) describes a spectrometer secondary reference calibration. The spectrometer is designed to perform a measurement on a sample. To perform a diagnostic measurement, secondary reference samples are provided in a turret or paddle inserted mechanically into a measurement chamber of the spectrometer.

SUMMARY

An apparatus is disclosed for performing a light-absorption measurement on a test sample and a compliance measurement on at least one reference sample. The apparatus includes: an illumination system configured to direct light along a light path; a test sample receptacle holder configured to receive a test sample receptacle at a first position in the light path for a test sample measurement; a reference sample receptacle carrier including at least one holding area configured to receive a reference sample receptacle for a reference sample measurement; a detection system configured to detect light absorbed by a test sample during a test sample measurement and configured to detect light absorbed by a reference sample during a reference sample measurement; and an actuator connected to the reference sample receptacle carrier, the actuator configured to move the reference sample receptacle carrier to position a reference sample receptacle received in a respective one of the at least one holding area at a second position in the light path at a first point in time, and at a third position out of the light path at a second point in time. The first position and the second position are situated in the light path at different locations along the light path.

An apparatus is disclosed for performing a light-absorption measurement on a test sample and a compliance measurement on at least one reference sample. The apparatus includes: an illumination system configured to direct light along a light path; a test sample receptacle holder configured to receive a test sample receptacle at a first position in the light path for a test sample measurement; a reference sample receptacle carrier including at least one holding area receiving an empty reference sample receptacle for a reference sample measurement, the reference sample receptacle being configured to receive a reference sample; a detection system configured to detect light absorbed by a test sample during a test sample measurement and configured to detect light absorbed by a reference sample during a reference sample measurement; and an actuator connected to the reference sample receptacle carrier, the actuator configured to move the reference sample receptacle carrier to position the reference sample receptacle at a second position in the light path at a first point in time, and at a third position out of the light path at a second point in time. The first position and the second position are situated in the light path at different locations along the light path.

A method is disclosed for performing a light-absorption measurement on a test sample and a compliance measurement on at least one reference sample. The method includes: moving a reference sample receptacle carrier of an apparatus for performing a light-absorption measurement, to position a first reference sample receptacle received in a first holding area of the carrier at a second position in a light path; directing light from an illumination system of the apparatus to a detection system of the apparatus along the light path to perform a light-absorption measurement on a first reference sample contained in the first reference sample receptacle at the second position; moving the carrier to position the first reference sample receptacle out of the light path; placing a test sample receptacle in a test sample receptacle holder of the apparatus at a first position in the light path, the second position and the first position being situated in the light path at different locations along the light path; and directing light from the illumination system to the detection system along the light path to perform a light-absorption measurement on a test sample contained in the test sample receptacle at the first position.

BRIEF DESCRIPTION OF THE DRAWINGS

Other features and advantages disclosed herein will become more apparent from the following detailed description of exemplary embodiments when read in conjunction with the attached drawings, wherein.

DETAILED DESCRIPTION

Figure 1:
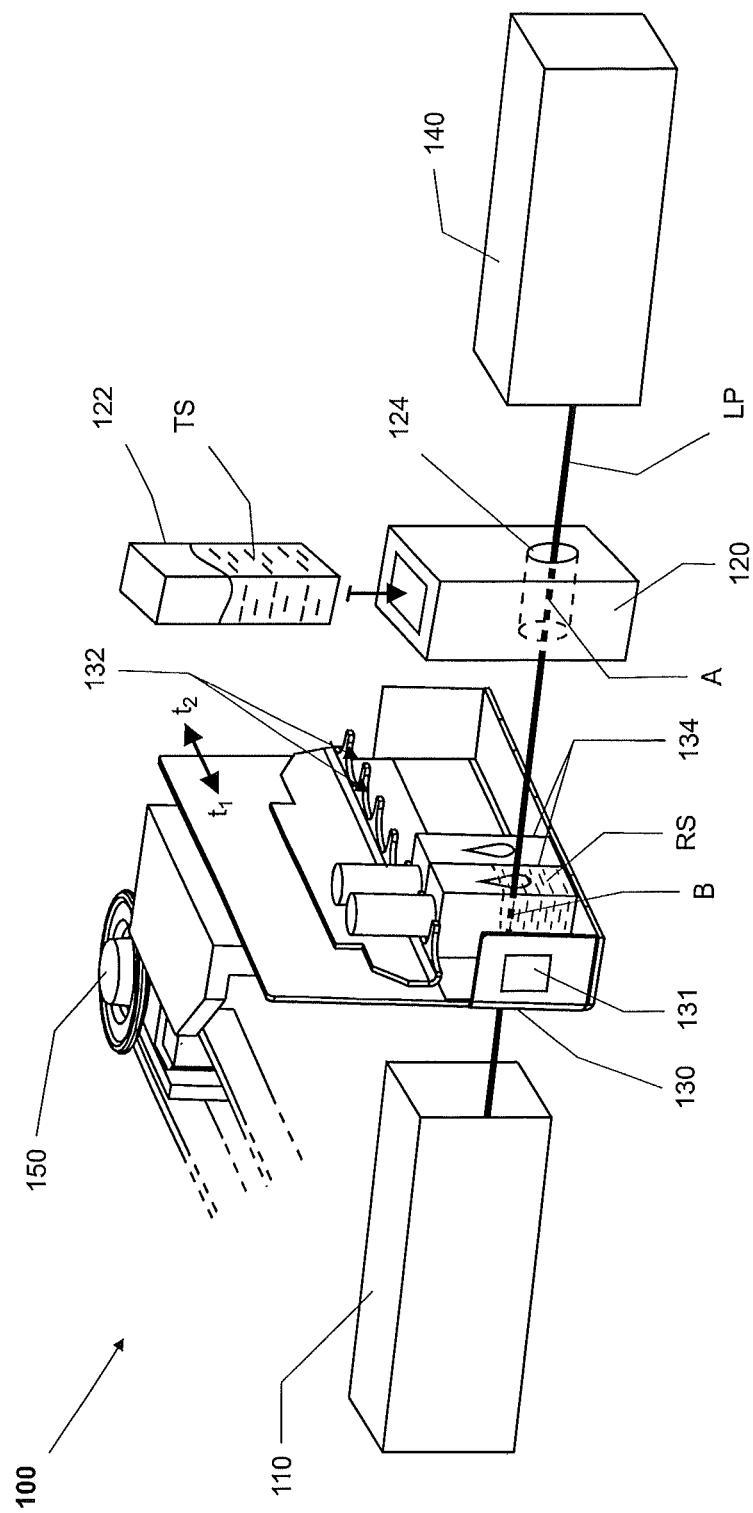
FIG. 1 shows an exemplary embodiment of an apparatus for performing a light-absorption measurement on a test sample and a compliance measurement on a reference sample.

FIG. 1 shows an exemplary embodiment of an apparatus 100 for performing a light-absorption measurement on a test sample TS and a compliance measurement on a reference sample RS. The apparatus 100 includes an illumination system 110 configured to direct light along a light path LP, a test sample receptacle holder 120 configured to receive a test sample receptacle 122 at a first position A in the light path LP for a test sample measurement, a reference sample receptacle carrier 130 including at least one holding area 132 configured to receive a reference sample receptacle 134 for a reference sample measurement, a detection system 140 configured to detect light absorbed by a test sample during a test sample measurement and configured to detect light absorbed by a reference sample RS during a reference sample measurement, and an actuator 150 connected to the reference sample receptacle carrier 130. The actuator 150 is configured to move the reference sample receptacle carrier 130 to position a reference sample receptacle 134 received in a respective one of the at least one holding area 132 at a second position B in the light path LP at a first point in time $t_1$, and at a third position (not labeled in FIG. 1) out of the light path LP at a second point in time $t_2$. The first position A and the second position B are situated in the light path LP at different locations along the light path LP. In an exemplary embodiment, moving the reference sample receptacle carrier 130 to position the reference sample receptacle 134 at a third position is achieved by moving the reference sample receptacle carrier to a parking position, in which all the reference sample receptacles 134 of the reference sample receptacle carrier 130 are out of the light path LP. An optical switch including a closed-loop feedback mechanism can be used to ensure that the various positions fall within predetermined tolerance parameters.

In an exemplary embodiment of the apparatus 100, because the first and second positions A and B are at different locations along the light path LP, the reference sample receptacle carrier 130 need not be removed from the apparatus 100 when making a measurement of a test sample TS located in the test sample receptacle holder 120. In addition, because the same light path LP is used for test sample measurements and reference sample measurements (i.e., the apparatus 100 is a single-beam system), the light path LP need not be redirected or changed between a test sample measurement and a reference sample measurement, thus leading to more accurate and reliable measurements.

In an exemplary embodiment of the apparatus 100, the reference sample receptacle carrier 130 includes two holding areas 132. Each holding area is configured to receive a respective one of two reference sample receptacles 134. The actuator 150 is configured to move the reference sample receptacle carrier 130 to position any one of two reference sample receptacles 134 received in a respective one the two holding areas 132 at the second position B.

Exemplary embodiments of a reference sample receptacle carrier 130 can include several holding areas 132. In an exemplary embodiment of the apparatus 100, the reference sample receptacle carrier 130 includes more than two holding areas 132, for performing compliance measurements in agreement with known standards. For example, the reference sample receptacle carrier 130 can include eight holding areas 132.

In an exemplary embodiment, the apparatus 100 is a spectrometer or spectrophotometer operating in the "UV/Vis" (ultraviolet-visible) range. In other exemplary embodiments the apparatus 100 is a spectrometer operating in either one, or in any combination of the following spectral ranges: UV/Vis, Vis (visible), MIR (mid infrared) and/or NIR (near infrared).

In exemplary embodiments of the apparatus 100, more than one reference sample receptacles 134 are placed in the reference sample receptacle carrier 130. For example, two reference sample receptacles 134 are used to measure photometric accuracy. One reference sample receptacle 134 contains a reference sample RS including a substance dissolved in a solvent, and the other reference sample receptacle 134 contains a reference sample RS including only the same solvent without the substance. A similar configuration of two reference sample receptacles 134 is used to measure stray light performance, and resolution. An air-filled reference sample receptacle 134 is used to measure stability, and a single reference sample receptacle 134 containing a reference sample RS in a solvent is used to measure wavelength accuracy. Other combinations of reference sample receptacles 134 containing reference samples RS in solvent, containing solvent without a reference sample RS, air-filled, empty, or filled with an organic composition, can be used to measure various properties of light or of the apparatus 100.

Figure 2:
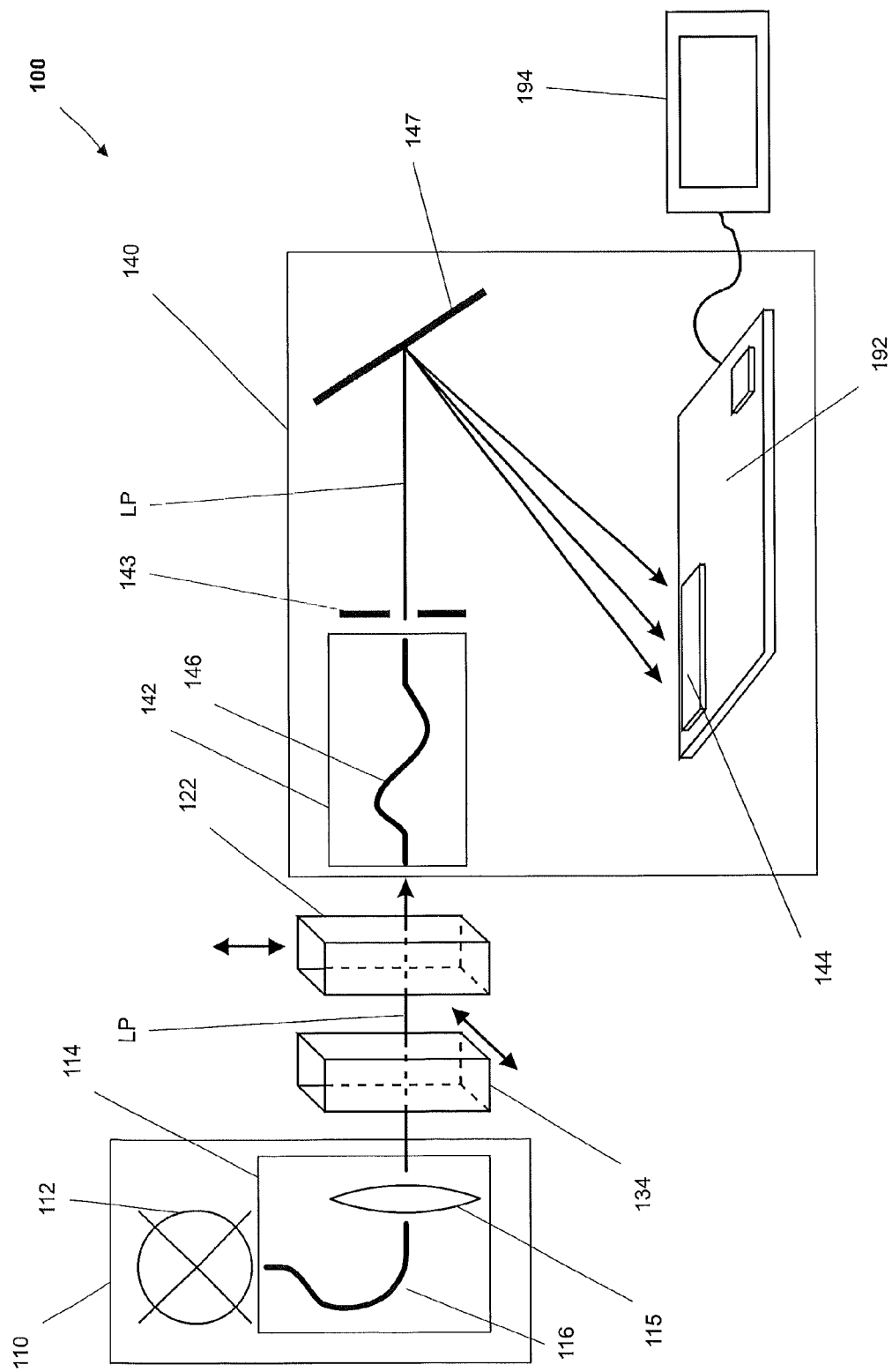
FIG. 2 shows exemplary embodiments of an illumination system and a detection system of an apparatus for performing a light-absorption measurement on a test sample and a compliance measurement on a reference sample.

FIG. 2 shows exemplary embodiments of an illumination system and a detection system of the apparatus 100. The illumination system 110 includes a light source 112 and first optical elements 114 on an emitting end of the apparatus 100. The first optical elements 114 include a first glass fiber 116. The illumination system 110 and the detection system 140 are configured such that light in a portion of the light path LP between the illumination system 110 and the detection system 140 is substantially collimated. In an exemplary embodiment, the optical characteristics of the glass fiber 116, optionally in combination with a collimator lens 115 (and/or a collimator mirror) at the end of the glass fiber 116, ensure that the beam is substantially collimated. Because the light is substantially collimated, measurements can be performed under similar light conditions at various positions (e.g., first and second positions A, B) along the light path between the illumination system 110 and the detection system 140. The detection system 140 includes second optical elements 142 on a receiving end of the apparatus 100, and a light detector 144. In an exemplary embodiment, an optical filter, such as for example an Order Sorting Filter (OSF filter), is disposed in the light path LP in front of the light detector 144. In an exemplary embodiment, the detector 144 includes a charge-coupled device (CCD) array detector, a linear CCD detector, a photo-diode array detector, and/or a complementary metal-oxide semiconductor (CMOS) detector, and/or another suitable detector known in the art or to be developed. In an exemplary embodiment, the detector 144 is disposed on a sensor chip 192 that includes a processor and non-transitory computer-readable memory and that is connected to a display 194 or via a computer for further processing to a display 194. The second optical elements 142 include a second glass fiber 146 and a dispersive element 147. In exemplary embodiments the dispersive element 147 includes a transmission grating, a grooved grating, a holographic grating and/or a prism, and/or another suitable dispersive element known in the art or to be developed. In exemplary embodiments the first and second optical elements 114 and 142 include optical elements such as lenses and mirrors to transmit the light along the light path LP from the light source 112 to the dispersive element 147 and the light detector 144 through an entrance slit 143. In an exemplary embodiment, a lens focuses collimated light onto the glass fiber 146. In exemplary embodiments, all optical elements in the light path LP, including for example the light source 112, the first and second optical elements 114 and 142, the glass fibers 116 and 146, the filter, and the detector 144, are optimized for the spectral range of the apparatus 100.

In an exemplary embodiment, the detection system 140 of the apparatus 100 includes a spectrograph, which includes an entrance slit 143, a dispersive element 147 and a light detector 144. The spectrograph can include a light-tight housing.

In an exemplary embodiment of the apparatus 100, the test sample receptacle holder 120 includes a through hole 124 through which the light path LP passes. More generally, the test sample receptacle holder 120 is configured such that when a test sample receptacle 122 is received in the test sample receptacle holder 120, a test sample TS in the test sample receptacle 122 is positioned at the first position A in the light path LP, and when the test sample receptacle holder 120 does not receive a test sample receptacle 122, the light path LP travels unobstructed by the test sample receptacle holder 120. In exemplary embodiments of the apparatus 100, the test sample receptacle holder 120 includes at least three poles with slots for positioning a test sample receptacle 122, or two members arranged with a gap between the two members, such that the light path LP passes through the test sample receptacle 122 but is unobstructed by the test sample receptacle holder 120. In exemplary embodiments, the test sample receptacle holder 120 includes a cuvette holder, a universal sample holder, and/or a test sample receptacle changer (automatic or manual), or other receptacle holders known in the art or to be developed.

In an exemplary embodiment of the apparatus 100, the reference sample receptacle carrier 130 includes non-transitory computer-readable medium 131. In an exemplary embodiment of the apparatus 100, the non-transitory computer-readable medium 131 includes read-only or read/write medium. The medium 131 stores data, such as, for example, certificate data associated with a reference sample RS contained in a reference sample receptacle 134, and/or standard certified values, tolerances, and a unique identifier. This data can be read by a sensor of the apparatus 100. This reduces the risks of human error associated with manually entering data related to the reference samples into the apparatus 100. In an exemplary embodiment of the apparatus 100, the non-transitory computer-readable medium 131 includes electrically erasable programmable read-only memory (EEPROM) and/or the memory of a radio-frequency identification (RFID) tag.

Figure 3:
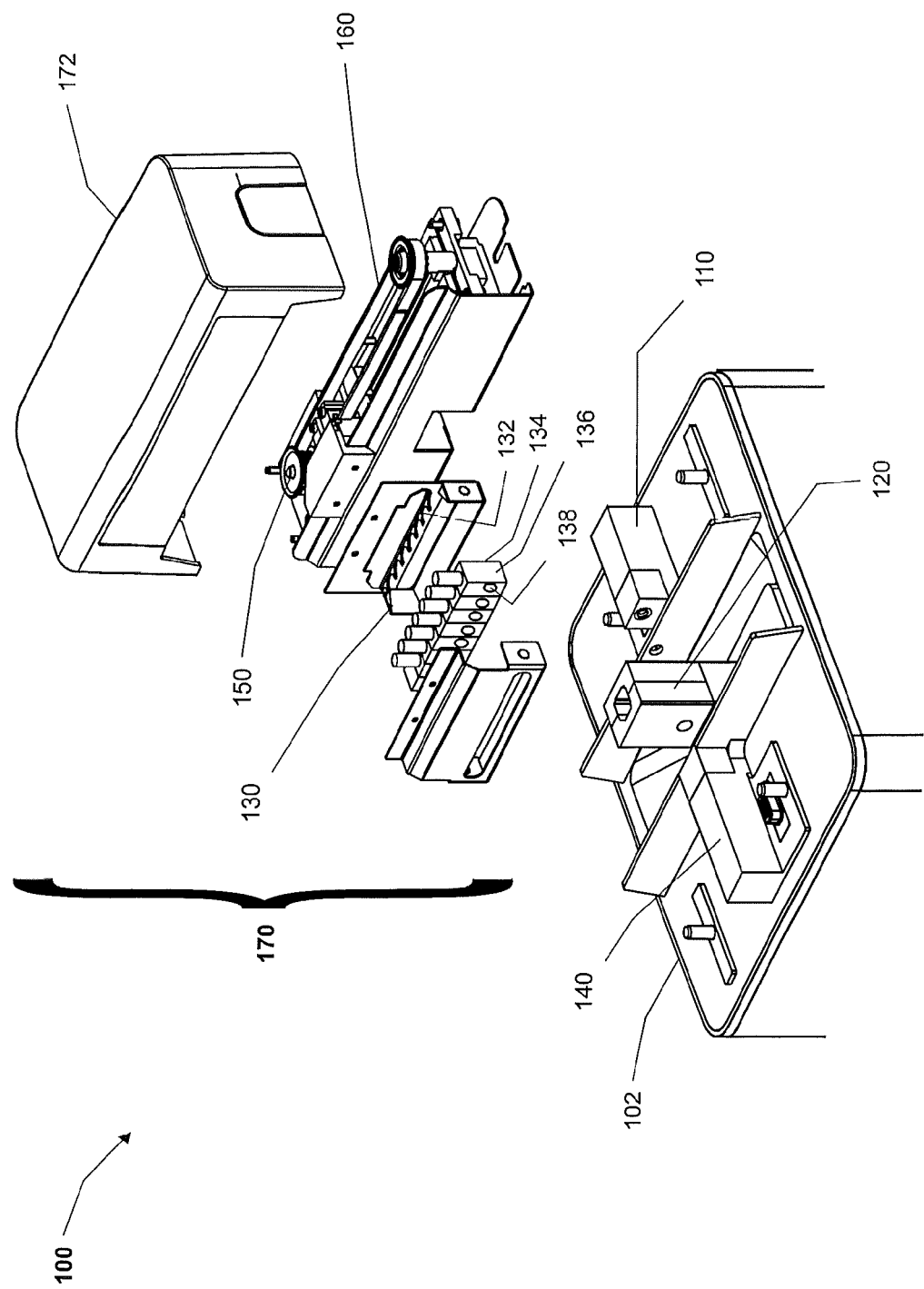
FIG. 3 shows an exploded view of an exemplary embodiment of a carrier assembly of an apparatus for performing a light-absorption measurement on a test sample and a compliance measurement on a reference sample.

As shown in FIG. 3, an exemplary embodiment of the apparatus 100 includes a linear conveyor 160 connecting the actuator 150 and the reference sample receptacle carrier 130. In exemplary embodiments of the apparatus 100, the linear conveyor 160 is a belt drive, a screw drive, or any other linear conveyor known in the art or to be developed.

An exemplary embodiment of the apparatus 100 includes a support member 102 coupled to the illumination system 110, the test sample receptacle holder 120 and the detection system 140. The apparatus 100 further includes a carrier assembly 170 that includes the reference sample receptacle carrier 130, the actuator 150, the linear conveyor 160, and a cover 172 attached to the linear conveyor 160. The linear conveyor 160 includes a linearly conveying portion and a support structure configured to attach the linear conveyor 160 to other elements of the apparatus 100. Placing the carrier 130 on the apparatus 100 using the carrier assembly 170 is less prone to human error than known methods, because it is less likely that the reference sample receptacles will be positioned incorrectly or that fingerprints will be present on optical surfaces. Additionally, the correct reference sample or reference samples in the correct concentration (according to a particular reference standard) can be used for a particular compliance measurement, and need not be sought in a laboratory, or freshly manufactured.

In exemplary embodiments of the apparatus 100, the carrier assembly 170 is configured to be removably attached to the support member. The cover 172 is configured to at least partially shield the reference sample receptacle carrier 130, the actuator 150 and the linear conveyor 160 from an environment outside of the apparatus 100 when the carrier assembly 170 is attached to the apparatus 100. It may be desirable to remove the carrier assembly 170 for recalibration, refilling, or recertification.

In exemplary embodiments of the apparatus 100, the carrier assembly 170 is configured to be removably attached to the support member 102 by a snap-fit attachment mechanism, a magnetic attachment mechanism, and/or a bolting mechanism.

In exemplary embodiments of the apparatus 100, the actuator 150 and the linear conveyor 160 are configured to have a linear precision of at least 10 micrometers. This increases the repeatability and accuracy of light-absorption measurements performed on reference samples.

In exemplary embodiments of the apparatus 100, the actuator 150, the linear conveyor 160 and the reference sample receptacle carrier 130 are arranged such that a reference sample receptacle 134 received in a respective holding area 132 is positioned out of the light path LP before the actuator 150 performs a predetermined movement and is positioned at the second position B after the actuator 150 performs a predetermined movement.

An exemplary embodiment of the apparatus 100 can be combined with a reference sample receptacle 134 received in a respective holding area 132. In an exemplary embodiment of the apparatus 100, the reference sample receptacle 134 is empty and can be filled by a user.

In exemplary embodiments of the apparatus 100, the reference sample receptacle 134 includes two opposite walls 136 (only one wall is visible in FIG. 3) each having a respective window 138 through which the light path LP passes when the reference sample receptacle 134 is positioned at the second position B. In an exemplary embodiment, light can only pass through the windows 138 of the reference sample receptacle 134, and the rest of the reference sample receptacle 134 is opaque. The windows 138 can be circular, rectangular, or of any other desired regular or irregular shapes.

In exemplary embodiments of the apparatus 100, one or both windows 138 are drop-shaped. The light path LP travels through the lower, wider portion of the drop-shaped window 138. A user can visually monitor the level of liquid in the reference sample receptacle 134 through the upper, narrower portion of the drop-shaped window 138. By monitoring the level of liquid inside the reference sample receptacle 134, the substance contained in the reference sample receptacle 134 can be replaced, or the reference sample receptacle 134 itself can be replaced, before the liquid level is too low for a compliance measurement (i.e., too low for light to pass through only the liquid during a light-absorption measurement). Alternatively, the window 138 can be round or oval. Preferably, the window is large enough for the light beam to pass through and small enough that only little ambient light penetrates the receptacle 134.

An exemplary embodiment of the apparatus 100 can be combined with a reference sample RS contained in the reference sample receptacle 134. The reference sample RS is selected to be used in a determination of wavelength accuracy of the apparatus, stray light performance of the apparatus, linearity of the apparatus, or resolution of the apparatus. The reference sample RS can conform to a regulatory standard. For example, the reference sample RS can conform to the standards issued by the American Society for Testing and Materials (ASTM), to the United States Pharmacopeial Convention (USP) reference standards, or to other standards known in the art or to be developed.

An exemplary embodiment of the apparatus 100 can be combined with a test sample receptacle 122 received in the test sample receptacle holder 120.

An exemplary embodiment of the apparatus 100 can be combined with a test sample receptacle 122 received in the test sample receptacle holder 120, and a test sample TS contained in the test sample receptacle 122.

In an exemplary embodiment of the apparatus 100, a reference sample receptacle carrier 130 containing reference sample receptacles 134 containing various combinations of reference samples RS and solvent(s) are configured so as not to be alterable by a user of the apparatus 100 performing light-absorption measurements.

In an exemplary embodiment of the apparatus 100, reference sample receptacles 134 containing various combinations of reference samples RS and solvent(s) are configured so as not to be alterable by a user of the apparatus 100 performing light-absorption measurements. The user can however place or remove individual reference sample receptacles 134 into and from a reference sample receptacle carrier 130, without altering the reference sample receptacles and the substance contained therein. By providing ready-filled reference sample receptacles 134, the reliability of light-absorption measurements and its reliability (relative to desired standards) are improved.

Figure 4:
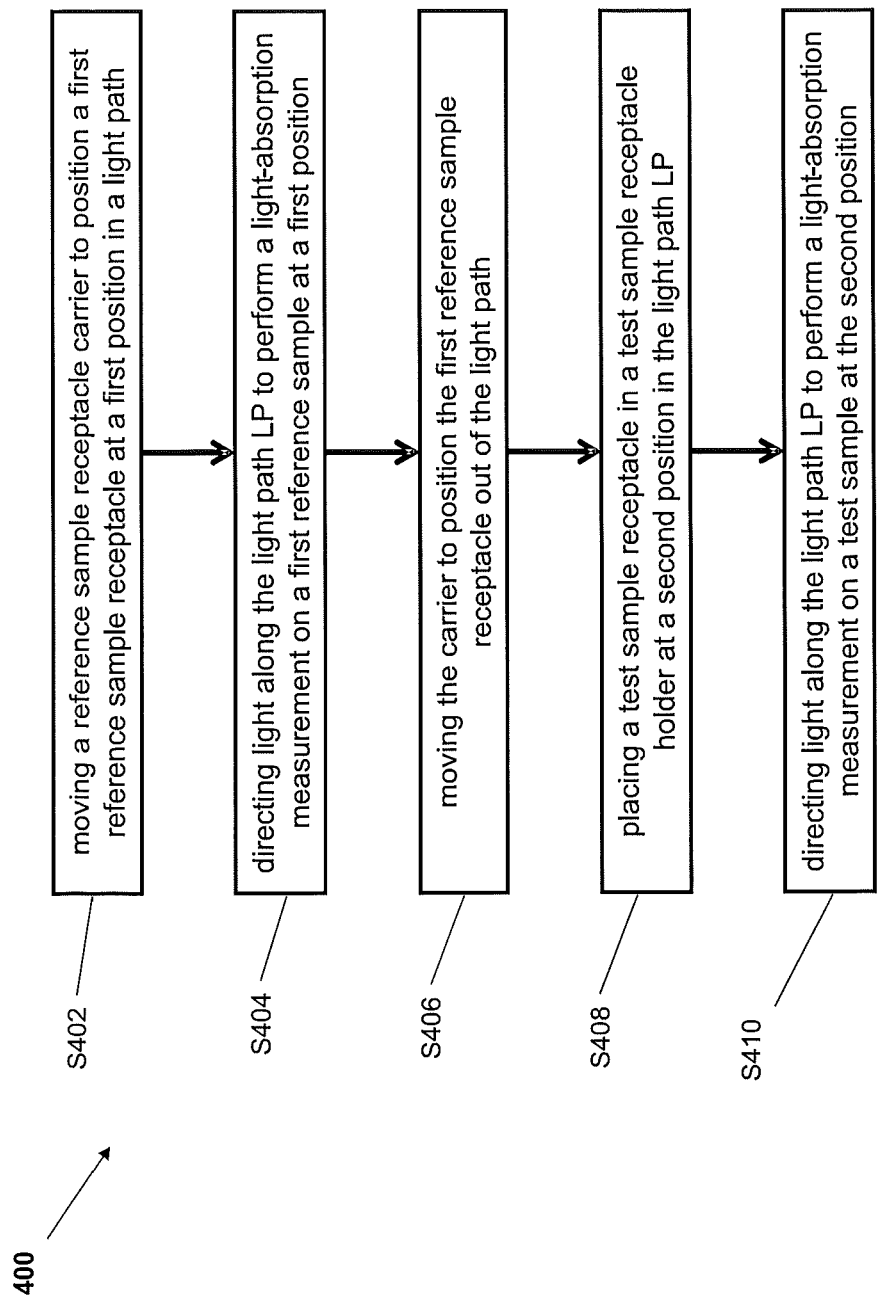
FIG. 4 shows a block diagram of an exemplary method for performing a light-absorption measurement on a test sample and a compliance measurement on at least one reference sample.

FIG. 4 shows a block diagram of an exemplary method 400 for performing a light-absorption measurement on a test sample TS and a compliance measurement on at least one reference sample RS. The method 400 includes moving a reference sample receptacle carrier 130 of an apparatus 100 for performing a light-absorption measurement, to position a first reference sample receptacle 134 received in a first holding area 132 of the carrier 130 at a second position B in a light path LP at step S402. The method 400 further includes directing light from an illumination system 110 of the apparatus to a detection system 140 of the apparatus along the light path LP to perform a light-absorption measurement on a first reference sample RS contained in the first reference sample receptacle 134 at the second position B at step S404. The method 400 further includes moving the carrier 130 to position the first reference sample receptacle 134 out of the light path LP at step S406, and placing a test sample receptacle 122 in a test sample receptacle holder 120 of the apparatus 100 at a first position A in the light path LP at step S408, wherein the second position B and the first position A are situated in the light path LP at different locations along the light path LP. The method 400 further includes directing light from the illumination system 110 to the detection system 140 along the light path LP to perform a light-absorption measurement on a test sample TS contained in the test sample receptacle 122 at the first position A at step S410.

An exemplary method 400 includes, before directing light from the illumination system 110 to the detection system 140 along the light path LP to perform the light-absorption measurement on the first reference sample RS contained in the first reference sample receptacle 134 at the second position B, ensuring that there is no test sample receptacle 122 received in the test sample receptacle holder 120. If a test sample receptacle 122 is received in the test sample receptacle holder 120, then the ensuring step includes removing the test sample receptacle 122 from the test sample receptacle holder 120. If no test sample receptacle 122 is received in the test sample receptacle holder 120, then the ensuring step includes proceeding to the next step in the method 400. The ensuring step can be performed before the moving step S402 or before the directing step S404. The ensuring step can be performed visually by a user. In the ensuring step, the test sample receptacle 122 can be removed manually by the user. For performing an exemplary method the first reference sample RS includes a reference substance dissolved in a solvent, a solvent, or air.

An exemplary method 400 includes moving the carrier 130 to position a second reference sample receptacle 134 received in a second holding area 132 of the carrier 130 at the second position B in the light path LP, and directing light from the illumination system 110 to the detection system 140 along the light path LP to perform a light-absorption measurement on a second reference sample RS contained in the second reference sample receptacle 134 at the second position B. For performing an exemplary method, the first reference sample RS includes a reference substance dissolved in a suitable solvent and the second reference sample RS includes only the solvent.

In an alternative exemplary method 400, the first reference sample receptacle 134 contains a reference sample RS dissolved in a solvent, and the second reference sample receptacle 134 contains the solvent only. The method further includes obtaining a first spectrum resulting from the light-absorption measurement of the reference sample RS with solvent, obtaining a second spectrum resulting from the light-absorption measurement of the solvent only, and obtaining a reference sample spectrum based on the first and second spectra. In exemplary methods, the reference sample spectrum is obtained by subtracting the second spectrum from the first spectrum, by calculating a ratio of the first and second spectra, or by other suitable methods. The method further includes analyzing the wavelength and/or the intensity of the reference sample spectrum. Wavelength can analyzed by obtaining the position of at least one peak or absorption maximum and determining therefrom the type of substance or class of substance in the reference sample RS. Intensity can be analyzed by obtaining the height of at least one peak or absorption maximum and determining therefrom the amount or concentration of substance in the reference sample RS. The method further includes determining whether compliance with a standard is achieved by comparing the results of the wavelength and/or intensity analysis to criteria associated with the standard. The method further includes storing data indicative of whether compliance is achieved in non-transitory computer-readable medium and/or displaying the data on the display 194. In an exemplary embodiment, the data is used to generate a compliance report.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An apparatus for performing a light-absorption measurement on a test sample and a compliance measurement on at least one reference sample, the apparatus comprising:
    an illumination system configured to direct light along a light path;
    a test sample receptacle holder configured to receive a test sample receptacle at a first position in the light path for a test sample measurement;
    a reference sample receptacle carrier including at least one holding area configured to receive a reference sample receptacle for a reference sample measurement;
    a detection system configured to detect light absorbed by a test sample during a test sample measurement and configured to detect light absorbed by a reference sample during a reference sample measurement;

an actuator connected to the reference sample receptacle carrier, the actuator configured to move the reference sample receptacle carrier to position a reference sample receptacle received in a respective one of the at least one holding area at a second position in the light path at a first point in time, and at a third position out of the light path at a second point in time;

a support member coupled to the illumination system, the test sample receptacle holder and the detection system;

a linear conveyor connecting the actuator and the reference sample receptacle carrier; and a carrier assembly that includes the reference sample receptacle carrier, the actuator, the linear conveyor, and a cover, wherein the carrier assembly is configured to be removably attached to the support member, wherein the cover is configured to at least partially shield the reference sample receptacle carrier, the actuator and the linear conveyor from an environment outside of the apparatus when the carrier assembly is attached to the support member, and wherein the first position and the second position are situated in the light path at different locations along the light path.

2. The apparatus for performing a light-absorption measurement on a test sample and a compliance measurement on at least one reference sample according to claim 1, wherein the reference sample receptacle carrier comprises:

at least two holding areas, the at least one holding area being one of the at least two holding areas, wherein each of the at least two holding areas is configured to receive a respective one of at least two reference sample receptacles, and wherein the actuator is configured to move the reference sample receptacle carrier to position any one of at least two reference sample receptacles received in a respective one of the at least two holding areas at the second position.

3. The apparatus for performing a light-absorption measurement on a test sample and a compliance measurement on at least one reference sample according to claim 1, wherein the illumination system comprises:

a light source; and first optical elements on an emitting end, the first optical elements comprising a first glass fiber, wherein the illumination system and the detection system are configured such that light in a portion of the light path between the illumination system and the detection system is substantially collimated.

4. The apparatus for performing a light-absorption measurement on a test sample and a compliance measurement on at least one reference sample according to claim 1, wherein the detection system comprises:

second optical elements on a receiving end, the second optical elements comprising a second glass fiber and a dispersive element; and a light detector.

5. The apparatus for performing a light-absorption measurement on a test sample and a compliance measurement on at least one reference sample according to claim 1, wherein the reference sample receptacle carrier comprises:

non-transitory computer-readable medium.

6. The apparatus for performing a light-absorption measurement on a test sample and a compliance measurement on at least one reference sample according to claim 1, wherein the cover is attached to the linear conveyor.

7. The apparatus for performing a light-absorption measurement on a test sample and a compliance measurement on at least one reference sample according to claim 1, wherein the carrier assembly is configured to be removably attached to the support member by an attachment mechanism selected from a set consisting of:

a snap-fit attachment mechanism;

a magnetic attachment mechanism; and a bolting mechanism.

8. The apparatus for performing a light-absorption measurement on a test sample and a compliance measurement on at least one reference sample according to claim 1, wherein the actuator and the linear conveyor are configured to have a linear precision of at least 10 micrometers.

9. The apparatus for performing a light-absorption measurement on a test sample and a compliance measurement on at least one reference sample according to claim 1, wherein the actuator, the linear conveyor and the reference sample receptacle carrier are arranged such that a reference sample receptacle received in a respective one of the at least one holding area is positioned out of the light path before the actuator performs a predetermined movement and is positioned at the second position after the actuator performs a predetermined movement.

10. The apparatus for performing a light-absorption measurement on a test sample and a compliance measurement on at least one reference sample according to claim 1, in combination with:

a reference sample receptacle received in a respective one of the at least one holding area.

11. The apparatus for performing a light-absorption measurement on a test sample and a compliance measurement on at least one reference sample according to claim 10, wherein the reference sample receptacle comprises:

two opposite walls each having a respective window through which the light path passes when the reference sample receptacle is positioned at the second position.

12. The apparatus for performing a light-absorption measurement on a test sample and a compliance measurement on at least one reference sample according to claim 11, wherein at least one of the windows is drop-shaped.

13. The apparatus for performing a light-absorption measurement on a test sample and a compliance measurement on at least one reference sample according to claim 10, in combination with:

a reference sample contained in the reference sample receptacle, wherein the reference sample is selected to be used in a determination of one of:

wavelength accuracy of the apparatus;

stray light performance of the apparatus;

linearity of the apparatus; or resolution of the apparatus.

14. The apparatus for performing a light-absorption measurement on a test sample and a compliance measurement on at least one reference sample according to claim 1, in combination with either:

a test sample receptacle received in the test sample receptacle holder; or the test sample receptacle received in the test sample receptacle holder further in combination with a test sample contained in the test sample receptacle.

15. An apparatus for performing a light-absorption measurement on a test sample and a compliance measurement on at least one reference sample, the apparatus comprising:

an illumination system configured to direct light along a light path;

a test sample receptacle holder configured to receive a test sample receptacle at a first position in the light path for a test sample measurement;

a reference sample receptacle carrier including at least one holding receiving an empty reference sample receptacle for a reference sample measurement, the reference sample receptacle being configured to receive a reference sample;

a detection system configured to detect light absorbed by a test sample during a test sample measurement and configured to detect light absorbed by a reference sample during a reference sample measurement; and an actuator connected to the reference sample receptacle carrier, the actuator configured to move the reference sample receptacle carrier to position the reference sample receptacle at a second position in the light path at a first point in time, and at a third position out of the light path at a second point in time;

a support member coupled to the illumination system, the test sample receptacle holder and the detection system;

a linear conveyor connecting the actuator and the reference sample receptacle carrier; and a carrier assembly that includes the reference sample receptacle carrier, the actuator, the linear conveyor, and a cover, wherein the carrier assembly is configured to be removably attached to the support member, wherein the cover is configured to at least partially shield the reference sample receptacle carrier, the actuator and the linear conveyor from an environment outside of the apparatus when the carrier assembly is attached to the support member, and wherein the first position and the second position are situated in the light path at different locations along the light path.

16. A method for performing a light-absorption measurement on a test sample and a compliance measurement on at least one reference sample, the method comprising:

moving a reference sample receptacle carrier of an apparatus for performing a light-absorption measurement, to position a first reference sample receptacle received in a first holding area of the carrier at a second position in a light path;

directing light from an illumination system of the apparatus to a detection system of the apparatus along the light path to perform a light-absorption measurement on a first reference sample contained in the first reference sample receptacle at the second position;

moving the carrier to position the first reference sample receptacle out of the light path;

placing a test sample receptacle in a test sample receptacle holder of the apparatus at a first position in the light path, wherein the second position and the first position are situated in the light path at different locations along the light path; and directing light from the illumination system to the detection system along the light path to perform a light-absorption measurement on a test sample contained in the test sample receptacle at the first position, a carrier assembly, including the reference sample receptacle carrier, an actuator, a linear conveyor and a cover, being attached to a support member coupled to the illumination system, the test sample receptacle holder and the detection system, such that the cover at least partially shields the reference sample receptacle carrier, the actuator and the linear conveyor from an environment outside of the apparatus, wherein the linear conveyor connects the actuator and the reference sample receptacle carrier.

17. The method for performing a light-absorption measurement on a test sample and a compliance measurement on at least one reference sample according to claim 16, the method comprising:

before directing light from the illumination system to the detection system along the light path to perform the light-absorption measurement on the first reference sample contained in the first reference sample receptacle at the second position, ensuring that there is no test sample receptacle received in the test sample receptacle holder.

18. The method for performing a light-absorption measurement on a test sample and a compliance measurement on at least one reference sample according to claim 16, the method comprising:

moving the carrier to position a second reference sample receptacle received in a second holding area of the carrier at the second position in the light path;

directing light from the illumination system to the detection system along the light path to perform a light-absorption measurement on a second reference sample contained in the second reference sample receptacle at the second position.

19. The method for performing a light-absorption measurement on a test sample and a compliance measurement on at least one reference sample according to claim 18, wherein the first reference sample comprises a substance dissolved in a solvent and the second reference sample comprises only the solvent, the method comprising:

obtaining a first spectrum resulting from the light-absorption measurement on the first reference sample contained in the first reference sample receptacle;

obtaining a second spectrum resulting from the light-absorption measurement on the substance contained in the second reference sample receptacle;

obtaining a reference sample spectrum based on the first and second spectra;

analyzing the wavelength and/or the intensity of the reference sample spectrum;

determining whether compliance with a standard is achieved; and storing data indicative of whether compliance is achieved in non-transitory computer-readable medium and/or displaying the data.

* * * * *